(12) United States Patent
Kismarton (10) Patent No.: US 9,063,035 B2
(45) Date of Patent: Jun. 23, 2015

(54) APPARATUS AND METHOD FOR LOAD TESTING A COUPON

(71) Applicant: The Boeing Company, Chicago, IL (US)

(72) Inventor: Max U. Kismarton, Renton, WA (US)

(73) Assignee: The Boeing Company, Chicago, IL (US)

( * ) Notice: Subject to any disclaimer, the term of this patent is extended or adjusted under 35 U.S.C. 154(b) by 95 days.

(21) Appl. No.: 13/908,606

(22) Filed: Jun. 3, 2013

(65) Prior Publication Data

US 2014/0352451 A1    Dec. 4, 2014

(51) Int. Cl.
*G01N 3/02* (2006.01)
*G01N 3/08* (2006.01)
*G01N 3/04* (2006.01)

(52) U.S. Cl.
CPC .. *G01N 3/02* (2013.01); *G01N 3/08* (2013.01); *G01N 3/04* (2013.01); *G01N 2203/0435* (2013.01)

(58) Field of Classification Search
CPC ............ G01N 3/04; G01N 2203/0067; G01N 2203/0075; G01N 2203/0282; G01N 3/02; G01N 3/08; G01N 2203/0435
USPC ................... 73/826, 855, 830, 831, 833, 788
See application file for complete search history.

(56) References Cited

U.S. PATENT DOCUMENTS

| | | | |
|---|---|---|---|
| 5,297,441 A * | 3/1994 | Smith et al. ..................... | 73/860 |
| 5,505,095 A | 4/1996 | Raymond | |
| 5,528,942 A * | 6/1996 | Baratta ........................... | 73/856 |
| 2004/0144180 A1* | 7/2004 | Imamura ......................... | 73/796 |
| 2006/0070452 A1* | 4/2006 | Bohlmann et al. .............. | 73/800 |
| 2007/0107534 A1 | 5/2007 | Lemmer et al. | |
| 2007/0227259 A1* | 10/2007 | Alba ............................... | 73/831 |
| 2009/0007689 A1* | 1/2009 | Kawano .......................... | 73/788 |
| 2009/0007692 A1* | 1/2009 | Ferguson et al. ............... | 73/856 |

FOREIGN PATENT DOCUMENTS

DE        10 2005 058582        6/2007

OTHER PUBLICATIONS

English Machine Translation of DE102005058582, Bernhard, Jun. 14, 2007.*
Extended European Search Report, App. No. 14170412.2 (2014).

* cited by examiner

*Primary Examiner* — Lisa Caputo
*Assistant Examiner* — Philip Cotey
(74) *Attorney, Agent, or Firm* — Walters & Wasylyna LLC (57) ABSTRACT

An apparatus for load testing a coupon may include a test frame and a pair of spaced apart load balancing assemblies connected to the test frame, each load balancing assembly of the pair of load balancing assemblies including a load leveling mechanism connected to the test frame and a plurality of spaced apart load plates, each load plate of the plurality of load plates having a first end pivotably connected to the load leveling mechanism and a second end, the second end of each load plate including a friction holder configured to frictionally engage an end of the coupon, wherein at least one load balancing assembly of the pair of load balancing assemblies is movable along an axis of movement with respect to an opposed load balancing assembly to communicate a load to the coupon.

15 Claims, 10 Drawing Sheets

APPARATUS AND METHOD FOR LOAD TESTING A COUPON

FIELD

The present disclosure is generally related to material load testing and, more particularly, to an apparatus and method for load testing a coupon of sample material.

BACKGROUND

Information related to strength properties and behavior of a material is crucial in component and part design, particularly in the aerospace industry. Typically such information is found through load testing a sample of the material and observing its behavior under various load conditions. For example, a small sample of material, known as a coupon, may be loaded with a tensile load or a compressive load and tested to destruction.

Coupons are typically fabricated to include particular features configured for attachment to a testing jig or machine. For example, several tabs are built on the coupon and holes are drilled through the tabs, which are bolted to the test jig. Once the test is complete, the coupon must be unbolted and removed from the test jig. Thus, the process of testing a new material can be time intensive and costly. For example, the process of fabricating and testing coupons can take between 2 and 6 months.

With the development of new composite materials, the time and cost associated with testing the composites and various configurations of composites can be prohibitive. For example, composite structures have many different combinations of layering will require orders of magnitude more coupon testing.

Accordingly, those skilled in the art continue with research and development efforts in the field of material load testing.

SUMMARY

In one embodiment, the disclosed apparatus for load testing a coupon may include a test frame and a pair of spaced apart load balancing assemblies connected to the test frame, each load balancing assembly of the pair of load balancing assemblies including a load leveling mechanism connected to the test frame and a plurality of spaced apart load plates, each load plate of the plurality of load plates having a first end pivotably connected to the load leveling mechanism and a second end, the second end of each load plate including a friction holder configured to frictionally engage an end of the coupon, wherein at least one load balancing assembly of the pair of load balancing assemblies is movable along an axis of movement with respect to an opposed load balancing assembly to communicate a load to the coupon.

In another embodiment, the disclosed apparatus for load testing a coupon may include at least one load balancing assembly configured to retain an end of the coupon and communicate an axial load to the coupon upon movement along an axis, the load balancing assembly including a load leveling mechanism and a plurality of spaced apart load plates, each load plate of the plurality of load plates having a first end and a second end, the first end being pivotably connected to the load leveling mechanism and the second end including a friction holder configured to frictionally engage an end of the coupon.

In another embodiment, the disclosed apparatus for load testing a coupon may include at least one load balancing assembly configured to retain an end of the coupon and communicate an axial load to the coupon upon movement along an axis, the load balancing assembly including a load leveling mechanism and a plurality of spaced apart load plates, each load plate of the plurality of load plates having a first end and a second end, the first end being pivotably connected to the load leveling mechanism and the second end including a friction holder configured to frictionally engage an end of the coupon, the friction holder may include adjustably connected to the load plate within an opening, the grip wedge being configured to frictionally engage a substantially planar surface of the coupon, an adjusting mechanism configured to position the grip wedge within the opening, and a connector configured to interconnect the grip wedge and the load plate, the connector being configured to allow movement of the grip wedge with respect to the load plate.

In another embodiment, disclosed is a method for load testing a coupon, the method may include the steps of: (1) providing a test coupon, (2) providing a pair of load balancing assemblies, each load balancing assembly including a load leveling mechanism and a plurality of spaced apart load plates, each load plate of the plurality of load plates including a first end and a second end, the first end being pivotably connected to the load leveling mechanism and the second end including a friction holder, (3) connecting the coupon between the pair of load balancing assemblies, and (4) applying a load to the coupon.

Other embodiments of the disclosed apparatus and method for load testing a coupon will become apparent from the following detailed description, the accompanying drawings and the appended claims.

DETAILED DESCRIPTION

The following detailed description refers to the accompanying drawings, which illustrate specific embodiments of the disclosure. Other embodiments having different structures and operations do not depart from the scope of the present disclosure. Like reference numerals may refer to the same element or component in the different drawings.

Figure 1:
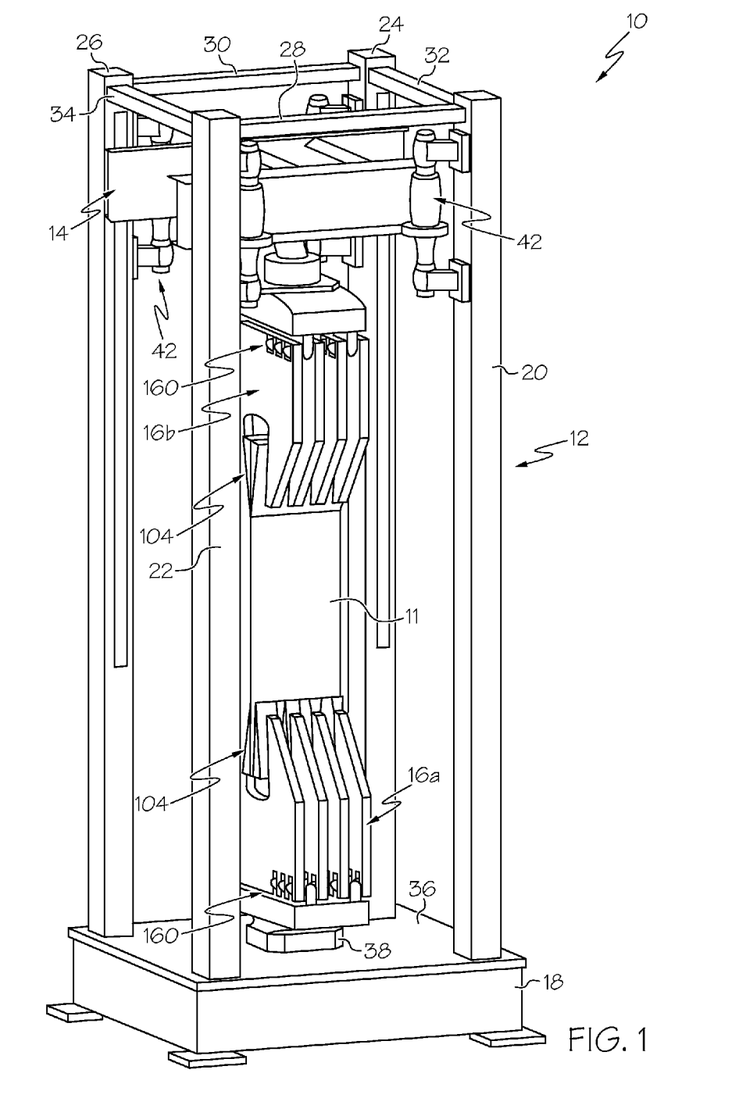
FIG. 1 is a front and side perspective view of one embodiment of the disclosed apparatus for load testing a coupon.

Referring to FIG. 1, the disclosed apparatus for load testing a coupon, generally designated 10, may include a test frame 12, at least one load assembly 14, and a pair of load balancing assemblies 16a, 16b (generally, a balancing assembly 16). The apparatus 10 may be used in load testing of a coupon 11 to determine the behavior of the material or materials forming the coupon 11 under both compression and tensile loads, particularly under peak load conditions. Each load balancing assembly 16 may include a friction holder 104 configured to grip and hold an end of the coupon 11 through friction and a mechanical load leveling mechanism 160 configured to distribute a substantially even load across a width of the coupon 11.

A coupon 11 is a small sample of material that may be tested to destruction to measure the strength properties of the material. As an example, the coupon 11 may be a 20-inch by 60-inch strip of sample material. However, the coupon 11 may have any geometric shape and dimensions.

Figure 2:
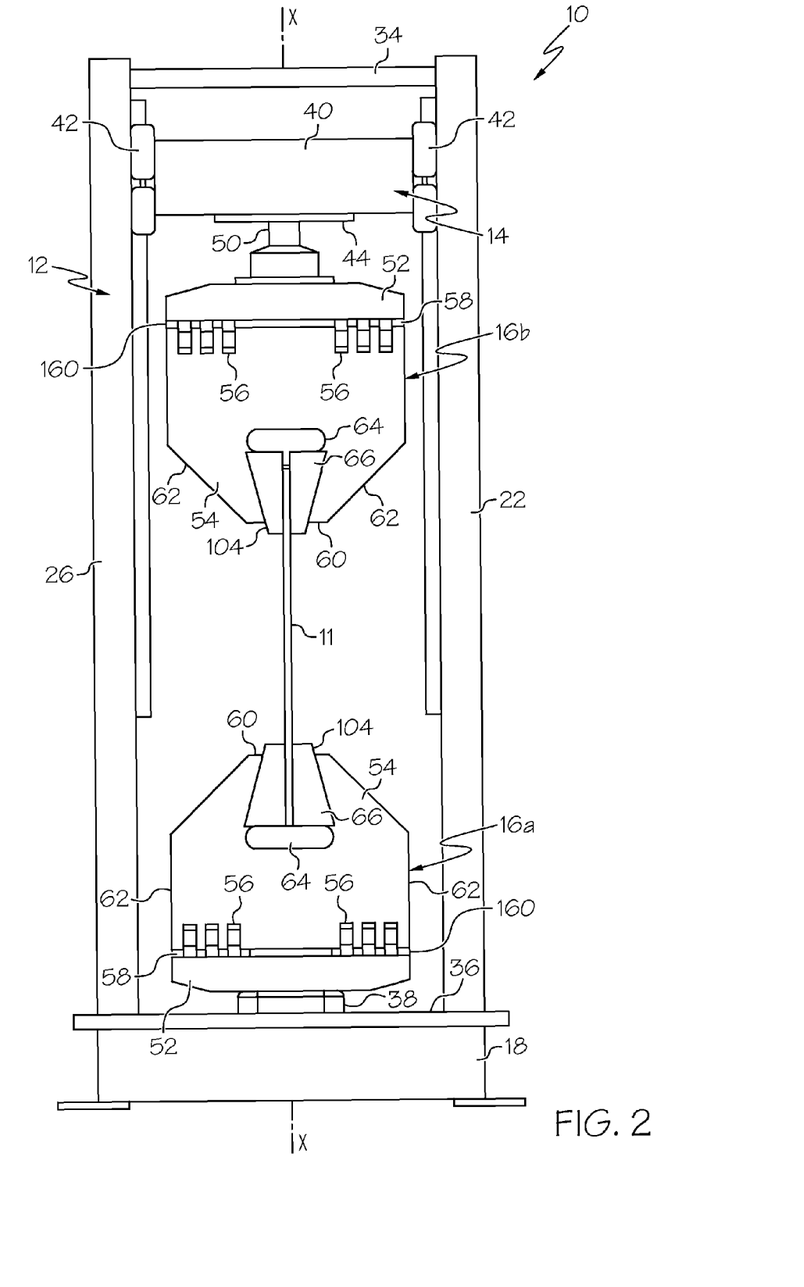
FIG. 2 is a side elevational view of the disclosed apparatus for load testing a coupon.

The pair of load balancing assemblies 16a, 16b may securely retain the coupon 11 at two opposing ends. Each of the load balancing assemblies 16a, 16b may be suitably sized to grip and retain a correspondingly sized coupon 11. The load assembly 14 may deliver a load (e.g., tensile or compression load) to the coupon 11 by moving at least one of the load balancing assemblies 16 along a single axis X (FIG. 2).

The test frame 12 may include a base member 18 configured to support the frame 12 in a generally vertical orientation in relation to a support surface. The base member 18 may have a generally square or rectangular shape, although any other geometric shapes are also contemplated.

A plurality of frame members may be connected to the base member 18 to define the test frame 12. For example, four spaced apart frame members may define a generally rectangular test frame 12. The four frame members may include a first frame member 20, a second frame member 22, a third frame member 24, and a fourth frame member 26. Each frame member 20, 22, 24, 26 may include a first end (e.g., lower end) rigidly connected to the base member 18. For example, the first end of each frame member 20, 22, 24, 26 may be rigidly connected at or near each corner of the base member 18.

A plurality of frame support members may interconnect between the frame members. For example, four frame support members may extend between second ends (e.g., upper ends) of parallel frame members. The four frame support members may include a first frame support member 28, a second frame support member 30, a third frame support member 32, and a fourth frame support member 34. The first frame support member 28 may interconnect between the second end of the first frame member 20 and the second end of the second frame member 22. The second frame support member 30 may interconnect between the second end of the third frame member 24 and the second end of the fourth frame member 26. The third frame support member 32 may interconnect between the second end of the first frame member 20 and the second end of the third frame member 24. The fourth frame support member 34 may interconnect between the second end of the second frame member 22 and the second end of the fourth frame member 26.

The test frame 12, including the base member 18, the frame members 20, 22, 24, 26, and the frame support members 28, 30, 32, 34 may be made from any suitably rigid and durable material. For example, the support base 18 and the frame members 20, 22, 24, 26 may be made from structural steel tube, steel channel, or steel I-beam. The frame support members 28, 30, 32, 34 may be made from steel rod or steel tube or channel. In the illustrated embodiment, the members of the test frame 12 may be welded together, however, other embodiments may use other materials and other methods of combining the members of the test frame 12. Alternatively, the test frame 12 may be an integral frame body instead of being formed of component members.

A first (e.g., lower) load balancing assembly 16a may be connected to the base member 18. For example, the first load balancing assembly 16a may be rigidly connected to a central or middle position of the base member 18. In one implementation of the disclosed apparatus 10, the base member 18 may include a base platform 36. The base platform 36 may be any suitably rigid and durable member or members suitable for connection of the first load balancing assembly 16a. For example, the base platform 36 may be a steel panel having at least one substantially planar major surface configured to support the first load balancing assembly 16a in fixed position. As another example, the base platform 36 may be a plurality of cross-frame members extending between the corners of the base member 18.

The base member 18 may include a first coupling 38 configured to connect to the first load balancing assembly 16a. For example, the first coupling 38 may be connected about a center or middle of the base platform 36. The first coupling 38 may be any suitable rigid mechanical coupling device, for example, the first coupling 38 may be collar, a sleeve, or a clamp. In this regard, the first coupling 38 may be any type of connection point or attachment point by which the first load balancing assembly 16a may be connected to the base member 18.

Figure 3:
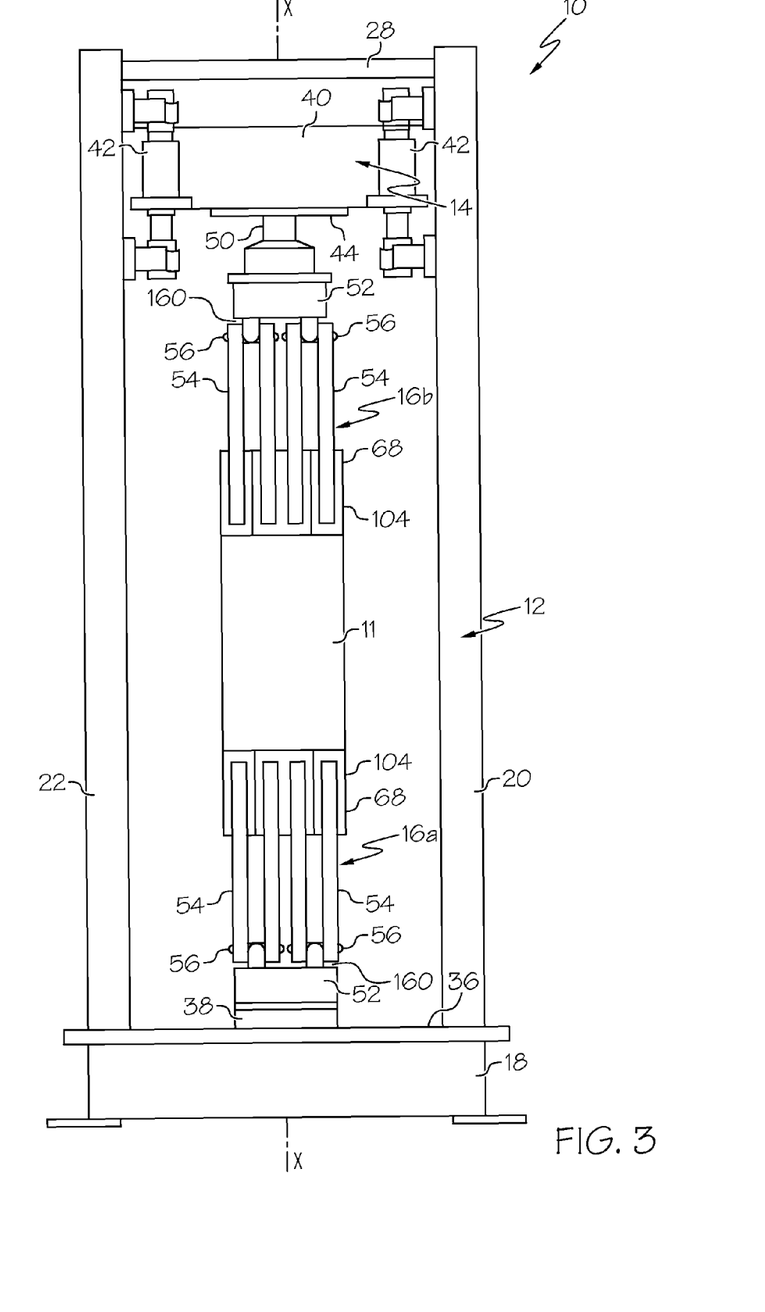
FIG. 3 is a front elevational view of the disclosed apparatus for load testing a coupon.

Referring to FIGS. 2 and 3, the load assembly 14 may include a load platform 40 operably connected to the frame members 20, 22, 24, 26. The load platform 40 may be movable in two opposing directions along the axis X. The load platform 40 may be any suitably rigid and durable member or members suitable for connection of a second (e.g., upper) load balancing assembly 16b.

For example, the load platform 40 may include a steel panel having at least one substantially planar major surface configured to support the second load balancing assembly 16b in fixed position. As another example, the load platform 40 may include a plurality of cross-frame members extending between the frame members 20, 22, 24, 26. As another example, the load platform 40 may include a pair of load supports, each load support extending between and movably connected to parallel pairs of frame members 20, 22, 24, 26 and a panel or cross-frame members connected between the pair of load supports.

The load assembly 14 may include at least one drive assembly 42. The drive assembly 42 may be any suitable linear actuation drive configured to move the load assembly 14 in at least one of two directions (e.g., up or down) along the axis X, such as a mechanical drive, a hydraulic drive, an electric drive, or the like. The drive assembly 42 may be a constant speed drive or a variable or adjustable speed drive.

In an example implementation, the drive assembly 42 may include at least one hydraulic cylinder containing a piston connected to a rod. For example the hydraulic cylinder may be rigidly connected to the test frame 12 and an end of the rod may be rigidly connected to the load platform 40. As another example, the hydraulic cylinder may be rigidly connected to the load platform 40 and an end of the rod may be rigidly connected to the test frame 12.

Movement of the piston inside the cylinder may cause the rod to move along the axis X and move the load assembly 14 with respect to the test frame 12 and thus, the second load balancing assembly 16b with respect to the first load balancing assembly 16a. Optionally, the load platform 40 may be moveably connected to each of the frame members 20, 22, 24, 26, for example by at least one roller disposed at each corner of the load platform 40.

In an example implementation, the drive assembly 42 may include at least one rack and pinion mechanism. For example, a rack may be connected to a surface of each frame member 20, 22, 24, 26. Each rack may be positioned parallel to the axis X. A rotary actuator, such as an electric motor or hydraulic rotary valve, may be connected to each corner of the load platform 40. A pinion gear may be operably connected to each rotary actuator and configured to engage an adjacent rack. Rotation of the pinion may cause the pinion to move along the rack parallel to the axis X and move the load assembly 14 with respect to the test frame 12 and thus, the second load balancing assembly 16b with respect to the first load balancing assembly 16a.

In another example implementation, the drive assembly 42 may include at least one worm drive. For example, a worm (e.g., a screw gear) may be connected to each frame member 20, 22, 24, 26. A worm gear may be rotatably connected to each corner of the load platform 40 and configured to engage the worm. Each worm may be positioned parallel to the axis X. A rotary actuator may be operably connected to at least one end of the worm. Rotation of the worm may cause the worm gear to move along the worm parallel to the axis X and move the load assembly 14 with respect to the test frame 12 and thus, the second load balancing assembly 16b with respect to the first load balancing assembly 16a.

The load assembly 14 may include a second coupling 44 configured to receivably connect to the second load balancing assembly 16b. For example, the second coupling 44 may be connected about a center or middle of the load platform 40. The second coupling 44 may be any suitable rigid mechanical coupling device, for example, the second coupling 44 may be collar, a sleeve, or a clamp. In this regard, the second coupling 44 may be any type of connection point or attachment point by which the second load balancing assembly 16b may be connected to the load assembly 14.

In another embodiment, the load platform 40 may be rigidly connected at a fixed position to the test frame 12, for example connected at each corner to the frame members 20, 22, 24, 26. The drive assembly 42 may be operably connected between the load platform 40 or the test frame 12 and the second load balancing assembly 16b. For example a hydraulic cylinder, containing a piston connected to a rod, may be rigidly connected to the load platform 40 or the test frame 12 and an end of the rod may be rigidly connected to the second load balancing assembly 16b. The second coupling 44 may be connected to the end of the rod for receivable connection to the second load balancing assembly 16b. Movement of the piston inside the cylinder may cause the rod to move along the axis X and move the second load balancing assembly 16b with respect to the load platform 40 and thus, the second load balancing assembly 16b with respect to the first load balancing assembly 16a.

In yet another embodiment, both the first 16a and second 16b load balancing assemblies may be moveable along the axis X. For example, a second load assembly (not shown) may be connected to the test frame 12 proximate the base member 18. The second load assembly may be substantially equivalent to the load assembly 14 described herein and may include a second drive assembly (not shown). The second drive assembly may be substantially equivalent to the drive assembly 42 described herein. The first load balancing assembly 16a may be connected to the second load assembly in any suitably manner, such that movement of the second load assembly along the axis X also moves the first load balancing assembly 16a with respect to the second load balancing assembly 16b.

Figure 4:
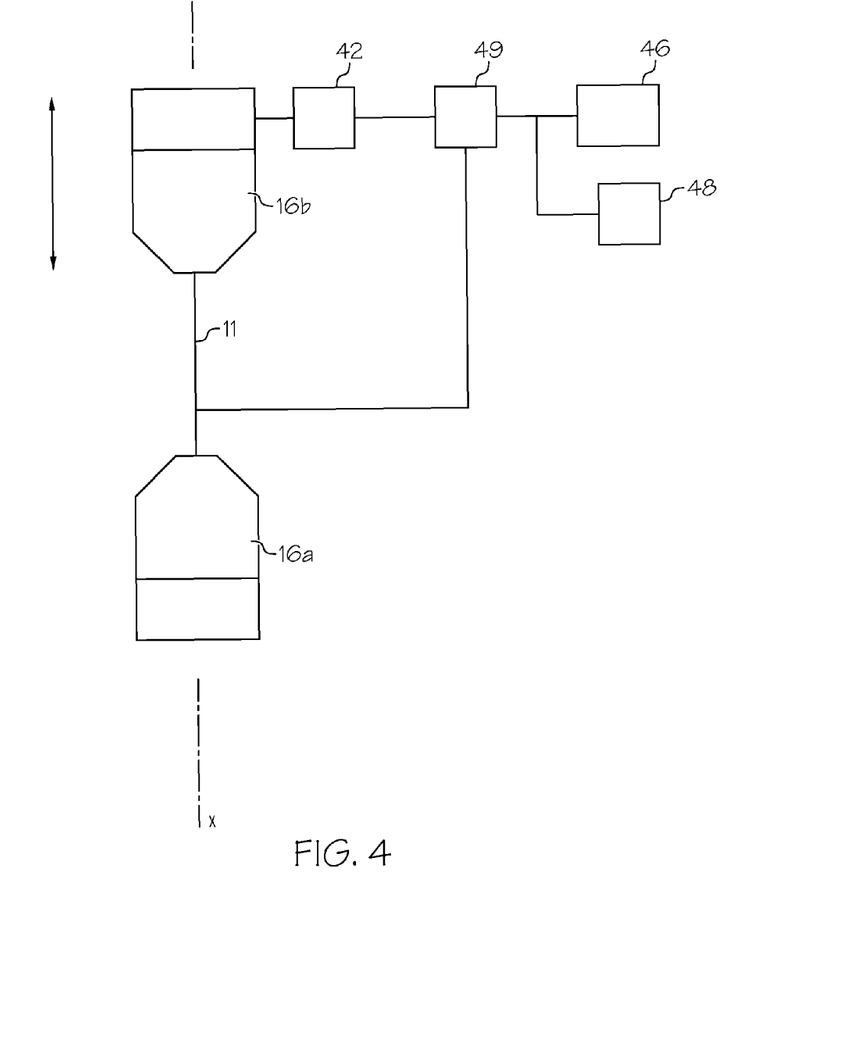
FIG. 4 is a block diagram illustrating the disclosed apparatus for load testing a coupon.

Referring to FIG. 4, the drive assembly 42, and optionally the second drive assembly, may be connected to an appropriate power source 46, such as an electrical power source or a hydraulic power source. A corresponding control unit 48 may be provided to receive input signals from an operator to control movement of the load balancing assemblies 16a, 16b and the load applied to the coupon 11. The control unit 48 may include a manual (e.g., push-button) user interface or a computer having a processor and programming stored on at least one computer readable medium.

Referring back to FIGS. 2 and 3, in an example construction, the load leveling mechanism 160 of each load balancing assembly 16a, 16b may include a stem 50, at least one arm 52, and a plurality of load plates 54 pivotably connected to the arm 52 by at least one lever 56. In general, load leveling mechanism 160 of each of the load balancing assemblies 16a, 16b may be configured as a whiffletree, or whippletree, to distribute a force (e.g., load) from the arm 52 evenly through the lever 56 or plurality of levers 56 to the plurality of plates 52 and across the width of the coupon 11.

In an example embodiment, as illustrated in FIGS. 1-3, the stem 50 of the first load balancing assembly 16a may be configured to be connected to the base member 18 (e.g., connected to the first coupling 38) and the stem 50 of the second load balancing assembly 16b may be configured to be connected to the load assembly 14 (e.g., connected to the second coupling 44). At least one arm 52 may be rigidly connected to the stem 50. Each lever 56 of the plurality of levers 56 may be pivotably connected at or near the center to the arm 52. An upper end of the load plate 54 may be pivotably connected at or near the ends of each of the plurality of levers 56.

Each load plate 54 may include two opposing major surfaces, a first edge 58, a second edge 60, and two opposing side edges 62. The major surfaces may be substantially planar and the width of the load plate 54 (e.g., distance between opposing side edges 62) may be greater than the thickness of the load plate 54. For example, the load plate 54 may be relatively thin compared to its length and width. Each of the plurality of load plates 54 may be positioned substantially parallel to an adjacent load plate 54 with minimal space between adjacent load plates 54. Each side edge 62 of the load plate 54 may taper inwardly from the first edge 58 to the second edge 62. Each load plate 54 may be made of any suitably rigid and durable material, such as steel or the like. The load plates 54 may be configured to grip the end of the coupon 11.

Optionally, at least one rigid member (not shown) may be interconnected between adjacent load plates 54 or may extend across the plurality of load plates 54 in order to control or prevent uncontrolled movement of the load plates 54 upon destruction (e.g., breaking) of the coupon 11 during load testing. For example, a steel rod may extend through all of the load plates 54.

Each load plate 54 may include at least one friction holder 104 disposed about the second edge 62. The friction holder 104 may be configured to frictionally engage and retain (e.g., grip) the end of the coupon 11 (FIG. 1). The friction holder 104 may be configured to contact opposing surfaces of the end of the coupon 11 and apply an initial frictional load upon the coupon 11. As the testing load is applied to the coupon 11 (e.g., by moving the load balancing assemblies 16 away from each other along the axis X) the frictional load upon the opposing surfaces of the end of the coupon 11 may increase to retain the coupon 11 within the load balancing assemblies 16.

The friction holder 104 may include at least one friction pad 140 (FIG. 5) and any suitable adjusting mechanism that can initially pre-load the ends of the coupon 11 by contacting the surface of the coupon 11 with the friction pad 140. The adjusting mechanism may increase the frictional load upon the ends of the coupon 11 as the testing load increases by allowing the friction pad 140 to move with respect to the load plate 54 as the coupon 11 is pulled away from the load balancing assembly 16.

As will described in more detail herein, an example construction of the friction holder 104 may include an opening, or cutout, 64 disposed about a middle of an end of the load plate 54 opposite the arm 52. For example, the opening 64 may extend from the second edge 62 toward the first edge 58. A pair of grip wedges 66 may be adjustably connected to the load plate 54 within the opening 64. The friction pad 140 may be connected to or integral to each grip wedge 66. The grip wedges 66 may be configured to grip and securely retain the end of the coupon 11 through frictional engagement with the friction pads 140 during load testing.

In the illustrated embodiment, a pair of arms 52 may be connected to stem 50 and a plurality of levers 56 may be connected to each of the pair of arms 52. For example, a first arm and a second arm may be connected to the stem 50. A first plurality of levers 56 may be connected to the first arm 52 and a second plurality of levers 56 may be connected to the second arm 52. Each lever 56 may include a first end and an opposed second end. A load plate 54 may be pivotably connected to each end of each lever 56. Each lever 56 may be spaced apart across first edges 58 of each adjacent pair of connected load plates 54. As illustrated in FIG. 2, the levers 56 may be connected near opposing ends of the first edge 58 of each load plate 54, although the levers 56 may be equally spaced apart across the entire first edge 58 of each load plate 54.

Figure 5:
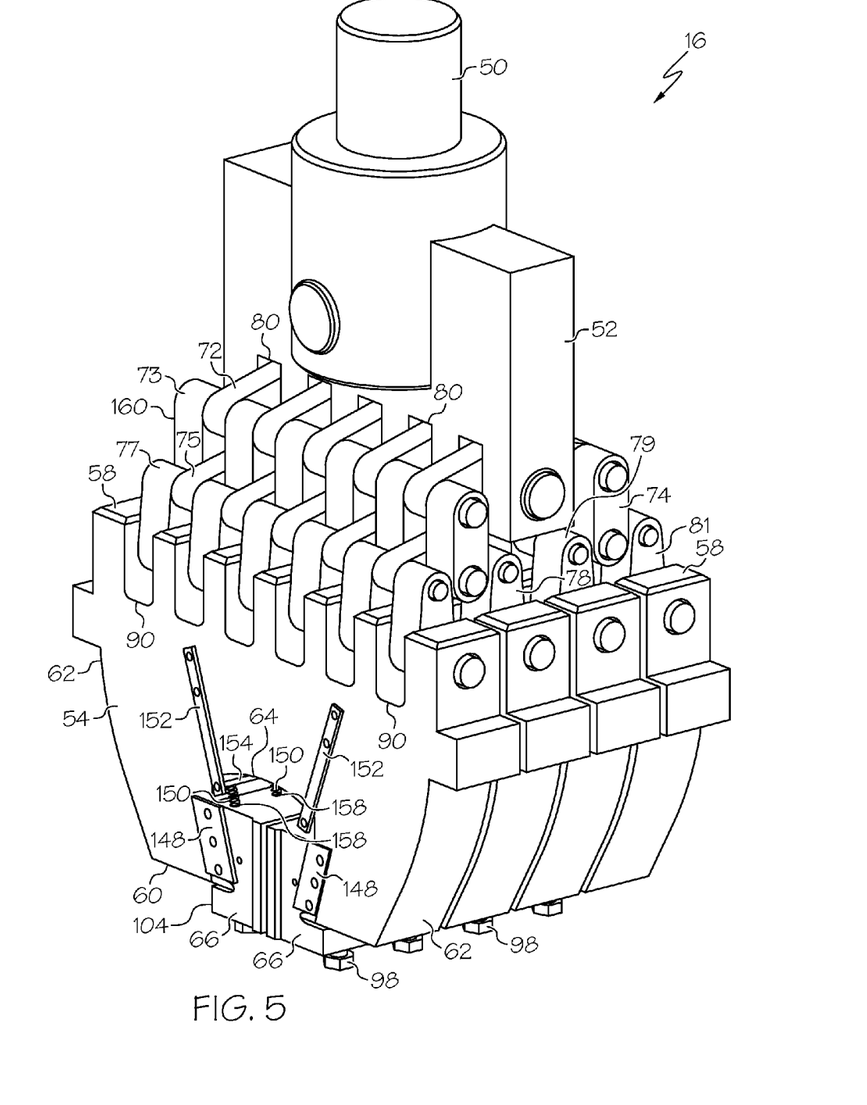
FIG. 5 is a front and side perspective view of one embodiment of the load balancing assembly of the disclosed apparatus for load testing a coupon.
Figure 7:
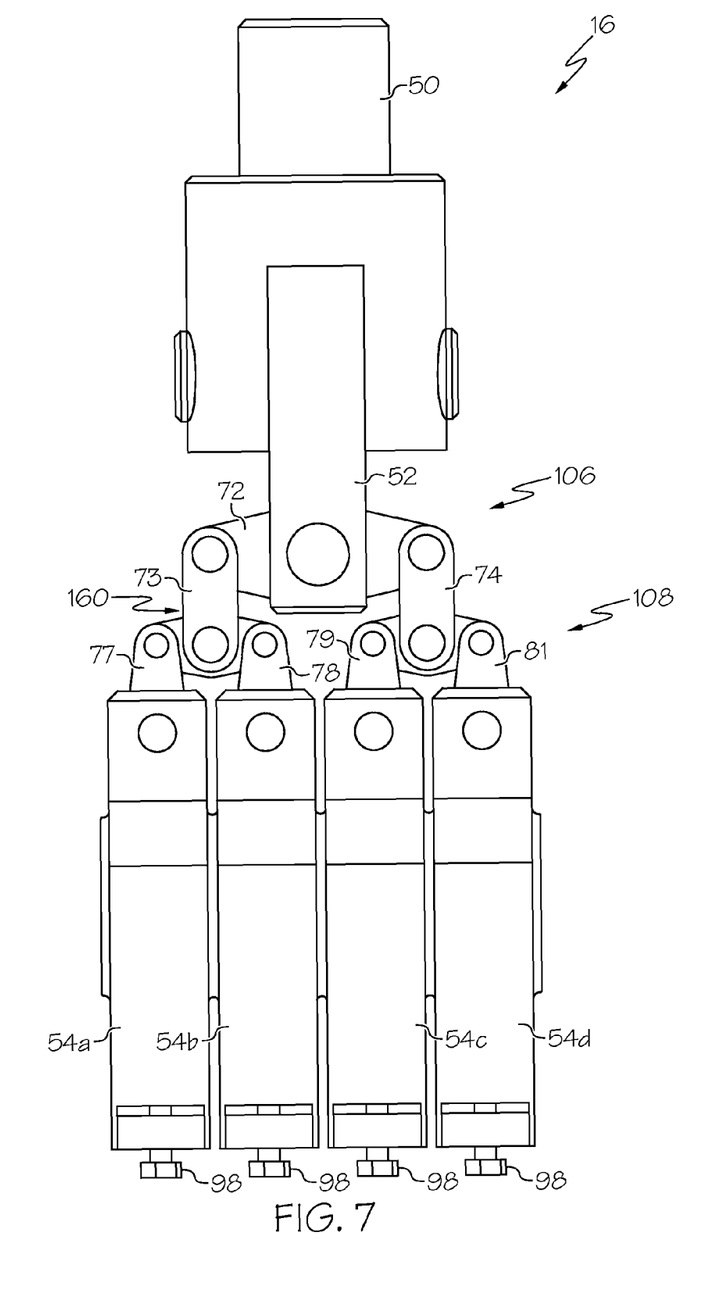
FIG. 7 is a front elevational view of the load balancing assembly.

Referring to FIGS. 5 and 7, in another example embodiment, the load balancing assembly 16 may be configured as a series of whiffletrees, or whippletrees, to evenly distribute a force (e.g. testing load) to the connected coupon 11 (FIG. 1). The load balancing assembly 16 may include a first level 106 (FIG. 7) and a second level 108 (FIG. 7).

At least one first lever 72 may be pivotably connected to the arm 52. At least one first linkage 73 may be pivotably connected to a first end of the first lever 72. At least one second linkage 74 may be pivotably connected to a second end of the first lever 72. The first lever 72, first linkage 73 and second linkage 74 may define the first level 106.

At least one second lever 75 may be pivotably connected to the first linkage 73. At lease one third lever 76 may be pivotably connected to the second linkage 74. At least one third linkage 77 may be pivotably connected to a first end of the second lever 75. At least one fourth linkage 78 may be pivotably connected to a second end of the second lever 75. At least one fifth linkage 79 may be pivotably connected to a first end of the third lever 76. At least one sixth linkage 81 may be pivotably connected to a second end of the third lever 76. The second lever 75, third lever 76, third linkage 77, fourth linkage 78, fifth linkage 79, and sixth linkage 81 may define the second level 108.

The plurality of load plates 54 may be pivotably connected to the linkages 77, 78, 79, 81 of the second level 108.

The stem 50 may include a cylindrical body having a first end configured to be received by the first coupling 38 or the second coupling 44 (FIG. 2). The stem 50 may be fastened to the corresponding coupling 38, 44 by any suitable mechanical fastener, such as a pin, bolt, or the like. The arm 52 may be rigidly connected to a second end of the stem 50. For example, the arm 52 may be mechanically fastened or welded to the stem 50. As another example, the stem 50 and the arm 52 may be integral (forming a unitary body).

Figure 6:
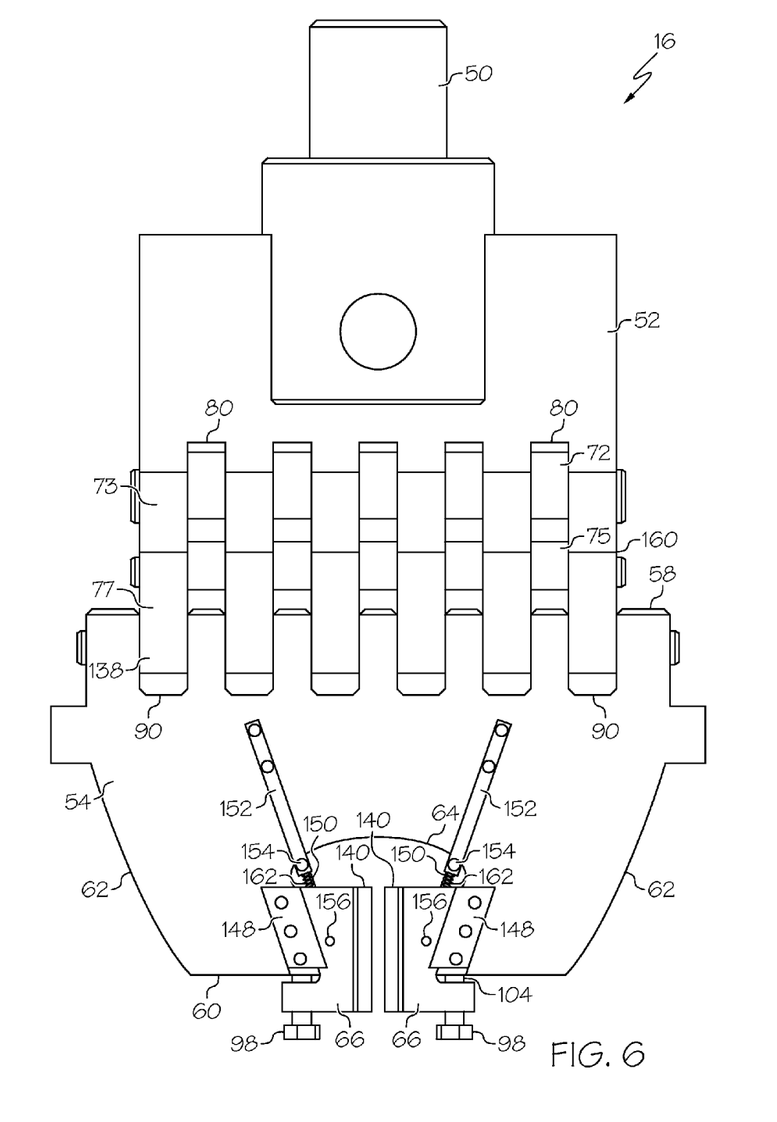
FIG. 6 is a side elevational view of the load balancing assembly.

Referring to FIGS. 5 and 6, the arm 52 may include at least one clevis feature 80. The clevis feature 80 may be configured to receive the first lever 72. The first lever 72 may be pivotably connected about or near the center within the clevis feature 80 at a first pivot point 82. For example, the first pivot point 82 may be a cylindrical rod or pin extending through each clevis feature 80 and associated first lever 72.

Figure 8:
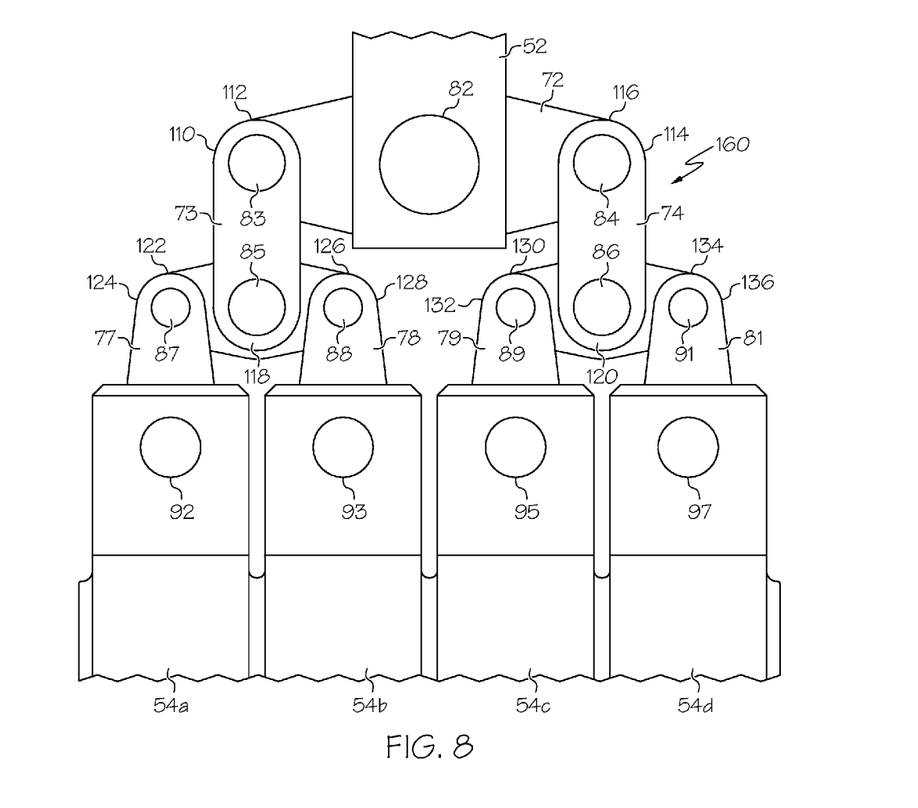
FIG. 8 is an enlarged front elevation view of the load balancing assembly.

Referring to FIGS. 5, 7 and 8, in an implementation of the example embodiment, the load balancing assembly 16 may include a plurality of first levers 72. A plurality of first linkages 73 may be pivotably connected at or near first ends of the plurality of first levers 72 and a plurality of second linkages 74 may be pivotably connected at or near second ends of the plurality of first levers 72. For example, a first end 110 of each first linkage 73 may be pivotably connected to a first end 112 of the first lever 72 at a second pivot point 83. A first end 114 of each second linkage 74 may be pivotably connected to an opposed second end 116 of the first lever 72 at a third pivot point 84.

The second pivot point 83 may be a cylindrical rod or pin extending through the first ends 110 of the plurality of first linkages 73 and the first ends 112 of the plurality of first levers 72. Depending upon the configuration of the load balancing assembly 16, the first levers 72 may be pivotably connected between first ends 110 of adjacent pairs of first linkages 73 (FIG. 5).

The third pivot point 84 may be a cylindrical rod or pin extending through the first ends 114 of the plurality of second linkages 74 and the second ends 116 of the plurality of first levers 72. Depending upon the configuration of the load balancing assembly 16, the first levers 72 may be pivotably connected between first ends 114 of adjacent pairs of second linkages 74 (FIG. 5).

A plurality of second levers 75 may be pivotably connected at or near the center to the plurality of first linkages 73. For example, a second end 118 of each first linkage 73 may be pivotably connected to the center of the second lever 75 at a fourth pivot point 85. The fourth pivot point 85 may be a cylindrical rod or pin extending through the second ends 118 of the plurality of first linkages 73 and the middles of the plurality of second levers 75. Depending upon the configuration of the load balancing assembly 16, the second levers 75 may be pivotably connected between second ends 118 of adjacent pairs of first linkages 73 (FIG. 5).

A plurality of third levers 76 may be pivotably connected at or near the center to the plurality of second linkages 73. For example, a second end 120 of each second linkage 74 may be pivotably connected to the center of the third lever 76 at a fifth pivot point 86. The fifth pivot point 86 may be a cylindrical rod or pin extending through the second ends 120 of the plurality of second linkages 74 and the middles of the plurality of third levers 76. Depending upon the configuration of the load balancing assembly 16, the third levers 76 may be pivotably connected between second ends 120 of adjacent pairs of second linkages 74 (FIG. 5).

A plurality of third linkages 77 may be pivotably connected at or near first ends 122 of the plurality of second levers 75. For example, a first end 124 of each third linkage 77 may be pivotably connected to the first end 122 of the second lever 75 at a sixth pivot point 87. The sixth pivot point 87 may be a cylindrical rod or pin extending through the first ends 124 of the plurality of third linkages 77 and the first ends 124 of the plurality of second levers 75. Depending upon the configuration of the load balancing assembly 16, the second levers 75 may be pivotably connected between first ends 124 of adjacent pairs of third linkages 77 (FIG. 5).

A plurality of fourth linkages 78 may be pivotably connected at or near opposed second ends 126 of the plurality of second levers 75. For example, a first end 128 of each fourth linkage 78 may be pivotably connected to the second end 126 of the second lever 75 at a seventh pivot point 88. The seventh pivot point 88 may be a cylindrical rod or pin extending through the first ends 128 of the plurality of fourth linkages 78 and the second ends 126 of the plurality of second levers 75. Depending upon the configuration of the load balancing assembly 16, the second levers 75 may be pivotably connected between first ends 128 of adjacent pairs of fourth linkages 78 (FIG. 5).

A plurality of fifth linkages 79 may be pivotably connected at or near first ends 130 of the plurality of third levers 76. For example, a first end 132 of each fifth linkage 79 may be pivotably connected to the first end 130 of the third lever 76 at an eighth pivot point 89. The eighth pivot point 89 may be a cylindrical rod or pin extending through the first ends 132 of the plurality of fifth linkages 79 and the first ends 130 of the plurality of third levers 76. Depending upon the configuration of the load balancing assembly 16, the third levers 76 may be pivotably connected between first ends 132 of adjacent pairs of fifth linkages 79 (FIG. 5).

A plurality of sixth linkages 81 may be pivotably connected at or near opposed second ends 134 of the plurality of third levers 76. For example, a first end 136 of each sixth linkage 81 may be pivotably connected to the second end 134 of the third lever 76 at a ninth pivot point 91. The ninth pivot point 91 may be a cylindrical rod or pin extending through the first ends 136 of the plurality of sixth linkages 81 and the second ends 134 of the plurality of third levers 76. Depending upon the configuration of the load balancing assembly 16, the third levers 76 may be pivotably connected between first ends 136 of adjacent pairs of sixth linkages 81 (FIG. 5).

Referring to FIG. 6, one load plate 54 of the plurality of load plates 54 may be pivotably connected to the second ends of each plurality of third 77, fourth 78, fifth 79, and sixth 81 linkages. For example, a first load plate 54*a* (FIG. 7) may be pivotably connected to second ends 138 of the plurality of third linkages 77 at a tenth pivot point 92. For example, the tenth pivot point 92 may be a cylindrical rod or pin extending through the clevis features 90 of the first load plate 54*a* and the second ends 138 of the fifth linkages 77.

While not visible in FIG. 6, it can be appreciated that a second load plate 54*b* may be pivotably connected to second ends of the plurality of fourth linkages 78 at an eleventh pivot point 93, a third load plate 54*c* may be pivotably connected to second ends of the plurality of fifth linkages 79 at a twelfth pivot point 95, and a fourth load plate 54*d* may be pivotably connected to second ends of the plurality of sixth linkages 81 at a thirteenth pivot point 97.

Referring to FIGS. 5 and 6, each load plate 54 may include a plurality of clevis features 90 disposed along the first edge 58. The plurality of clevis features 90 may be equally spaced along the first edge 58 of each load plate 54. For example, each clevis feature 90 of the first load plate 54*a* (FIG. 7) may be configured to receive the second end 138 of each fifth linkage 77.

While not visible in FIG. 6, it can be appreciated that the clevis features of the second load plate 54*b* (FIG. 7) may be configured to receive the second ends of each fourth linkage 78, the clevis features of the third load plate 54*c* (FIG. 7) may be configured to receive the second ends of each fifth linkage 79, and the clevis features of the fourth load plate 54*d* (FIG. 7) may be configured to receive the second ends of each sixth linkage 81.

The pivot connection between the of the load plates 54 and the plurality of linkages 77, 78, 79, 81 (e.g., at pivot points 92, 93, 95, 97) may allow each load plate 54 to self-balance and remain substantially parallel to the axis of movement X irrespective of the angularly rotated position of the plurality of second levers 75 or plurality of third levers 76. Due to the self-balancing nature of the load plates 54, each load plate 54 may introduce the distributed load to the coupon 11 parallel to a longitudinal axis of the coupon 11.

The load distributed to the arm 52 may be equally distributed throughout the plurality of levers and linkages to the load plates. For example, with each of the plurality of first levers 72 being connected at the center, the load distributed at the second end 116 of the plurality of first linkages 73 and the second ends 120 of the plurality of second linkages 74 may be one-half of the load distributed at the arm 52. With each of the plurality of second levers 75 being connected at the center to the plurality of second linkages 73, the load distributed at the second ends 138 (FIG. 6) of the plurality of third linkages 77 (and to the first load plate 54*a*) and the load distributed to the second ends (not shown) of the plurality of fourth linkages 78 (and to the second load plate 54*b*) may be one-half of the load distributed to the first ends 114 of the second linkages 73.

This balanced load distribution may be beneficial when utilizing the apparatus 10 in load testing coupons 11 (FIG. 1) of sample material. In certain fields, such as the aerospace industry, the stress level uniformity across the surface area of the testing coupon 11 during load testing must be within a predetermined range of acceptability.

It can be appreciated that the load distributed to the arm 52 may also be unequally distributed throughout the plurality of levers and linkages to the load plates. For example, with each of the plurality of first levers 72 being connected away from the center, the load distributed at the second ends 118 of the plurality of first linkages 73 and at the second ends 120 of the plurality of second linkages 74 may be a fraction of the load distributed at the arm 52 based on the distance from the center of the first lever 72. With each of the plurality of second levers 75 being connected away from the center, the load distributed at the second ends 138 (FIG. 6) of the plurality of third linkages 77 (and to the first load plate 54*a*) and at the second ends (not shown) of the plurality of fourth linkages 78 (and to the second load plate 54*b*) may be a fraction of the load distributed to the first ends 118 of the second linkages 73 based on the distance from the center of the second lever 75.

While the embodiment of the apparatus 10 illustrated in FIGS. 5-7 may include a first level 106 of levers 72 and linkages 73, 74 and a second level 108 of levers 75, 76 and linkages 77, 78, 79, 81 connected to the first level 106 and load plates 54 connected to the second level 108, more or less levels of levers and linkages may be used to distribute the load from the arm 52 to the load plates 54. For example, fewer levels of levers and linkages (e.g., at least one lever 56) may be used, as illustrated in FIGS. 1-3. As another example, additional levels of levers may be connected by linkages to adjacent (e.g., above or below) levels of levers. It can be appreciated that the number of levels of levers (e.g., the number of whippletree configurations) may determine the number of load plates 54 and the load distributed to each load plate 54.

Referring again to FIGS. 5 and 6, in the example construction of the friction holder 104, the friction pad 140 of each grip wedge 66 may include a substantially planar first surface 70 (FIG. 6) configured to contact an end surface of the coupon 11. The first surface 70 (e.g., friction pad 140) of first grip wedge 66a may be configured to face the first surface 70 (e.g., friction pad 140) of an opposing second grip wedge 66b (FIG. 6). The position of each grip wedge 66 within the opening 64 may be independently adjustable to close or open a gap 68 (FIG. 6) formed between opposing first surfaces 70 of the grip wedges 66.

The grip wedges 66 may be configured to securely retain (e.g., grip) the coupon 11 (FIG. 1) by a compressive force upon being adjusted to close the gap 68 and contact the coupon 11. Thus, the testing load may be applied from the grip wedges 66 (e.g., via the levers, linkages, and load plates 54) to the coupon 11 through friction. The first surface 70 of each grip wedge 66 may be configured to increase friction between the first surface 70 and the surface of the end of the coupon 11.

For example, the first surface 70 may be knurled or may include a high friction surface coating. As another example, the first surface 70 may include a plurality of barbs (not shown) configured to engage the end surface of the coupon 11 and resist movement of the coupon 11. Each of the barbs may extend outwardly at a non-zero angle with respect to the first surface 70. In an example implementation, the barbs may be disposed perpendicularly with respect to the first surface 70. In another implementation, the barbs may be disposed at a backwardly extending angle (e.g., opposite the direction of the testing load).

The grip wedges 66 may be suitably dimensioned to introduce the testing load to the coupon 11. For example, for use with a 20-inch by 60-inch coupon, the grip wedges 66 may be approximately twelve inches long in order to introduce 500 kips of load to the coupon 11. The grip wedges 66 may include a thickness substantially equivalent to the thickness of the load plate 54. Alternatively, the grip wedges 66 may include a thickness less than or greater than the thickness of the load plate 54. The Referring to FIG. 9, the load plate 54 may include sloped side surfaces 94 defining the opening 64. For example, the side surfaces 94 may be disposed a non-zero angle with respect the axis of movement X of the load balancing assembly 16 defining an inwardly tapered opening 64. As a non-limiting example, the side surfaces 94 may be disposed an eighteen-degree)(18° angle with respect the axis of movement X. Each grip wedge 66 may include a second surface 96 opposite the first surface 70 configured to contact the side surface 94 of the load plate 54 defining the opening 64.

Figure 9:
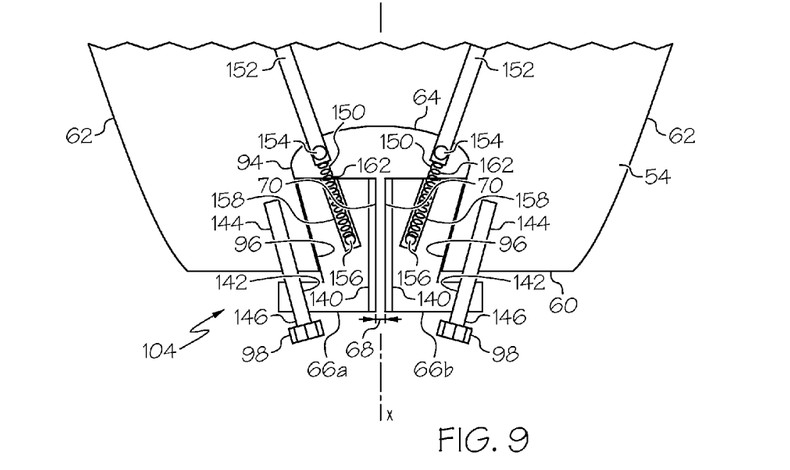
FIG. 9 is a side schematic view of an implementation of the friction holder of the disclosed apparatus for load testing a coupon.

Each grip wedge 66 may be independently positioned within the opening 64 upon the side surface 94 to adjust the position of the first grip wedge 66a, and thus the friction pad 140, with respect to the opposing second grip wedge 66b. For example, as each grip wedge 66 is positioned deeper within the opening 64, each grip wedge 66 may be located farther away from the opposing grip wedge 66. As another example, as each grip wedge 66 is positioned to extend out of the opening 64, each grip wedge 66 may be located close to the opposing grip wedge 66.

The grip wedges 66 may be configured such that the opposing first surfaces 70 may remain substantially parallel to one another and the axis X irrespective of the position of the grip wedge 66 with respect to the opening 64 or the opposing grip wedge 66. For example, the second surface 96 of each grip wedge 66 may be disposed at a non-zero angle (e.g., eighteen-degrees) with respect to the first surface 70. The angle between the first surface 70 and the second surface 96 of the grip wedge 66 may be substantially equivalent to the angle between the side surface 94 defining the opening 64 and the axis X.

As the grip wedges 66 are located closer to one another (e.g., by moving out of the opening 64), the gap 68 defined between opposing first surfaces 70 may decrease until the opposing first surfaces 70 contact one another or the end surfaces of the coupon 11. As the grip wedges 66 are located farther away from one another (e.g., by moving deeper within the opening 64), the gap 68 may increase. As such, the grip wedges 66 may be positioned to contact the coupon 11 (FIG. 1) upon placement of the coupon 11 within the gap 68 and adjustment of the grip wedges 66.

Each grip wedge 66 may include an adjusting mechanism 98 configured to pre-load the coupon 11 by adjusting the position of the grip wedge 66 within the opening 64 to place the end surfaces of the coupon 11 in contact with the friction pads 140. For example, the adjusting mechanism 98 may be a mechanical fastener engaged between the grip wedge 66 and the load plate 54. As another example, the adjusting mechanism 98 may be at least one hydraulic cylinder engaged between the load plate 54 and the grip wedge 66. Upon actuation of the adjusting mechanism 98, the grip wedge 66 may be positioned within the opening 64 to adjust the gap 68.

In an example construction, the adjusting mechanism 98 may be a bolt 146 extending through a lower end of the grip wedge 66 and into the lower end of the load plate 54. Each grip wedge 66 may include a tab on the lower end extending away from the first surface 70 toward the side edge 62 of the load plate 54. The bolt 146 may extend through the tab and into a bottom surface of the load plate 54.

The bolt 146 may be disposed at a non-zero angle with respect to the axis X. For example, the angle of the bolt 146 with respect to the axis X may be substantially equivalent to the angle of the second surface 96 of the grip wedge 66. As another example, the angle of the bolt 146 with respect to the axis X may be between about 35° and about 40°. As another example, the angle of the bolt 146 with respect to the axis X may be about 38°. Rotation of the bolt 146 may cause the grip wedge 66 to be positioned within the opening 64 to adjust the gap 68.

In an example implementation, the grip wedge 66 may include a threaded aperture 142 (e.g., through the tab) configured to receive and matingly engage with the bolt 146. The load plate 54 may include a smooth-bored aperture 144 disposed through the bottom surface (e.g., along the second edge 60). At least a portion of the shaft of the bold 146 may be received within the smooth-bored aperture 144. As the bolt 146 is rotated, the position of the bolt 146 remains constant within the smooth-bored aperture 144 and the grip wedge 66 moves along the threaded shaft of the bolt 146 and with respect to the load plate 54.

Referring again to FIGS. 5 and 6, each load plate 54 may include a pair of retainer plates 148 associated with each grip wedge 66. A retainer plate 148 may be fastened (e.g., bolted) to each opposing major surface of the load plate 54 proximate a side edge of the opening 64 and along side of the grip wedge 66. Each pair of opposing retainer plates 148 may restrict movement of the grip wedge 66 with respect to the load plate 54 in a direction perpendicular to the axis of movement X.

Referring to FIGS. 5, 6, and 9, each grip wedge 66 or pair of grip wedges 66 may also be movably connected to an associated load plate 54 by a grip wedge connector 162. For example, the grip wedge connector 162 may be at least one spring 150 connected between the grip wedge 66 and the load plate 54 (FIGS. 6 and 9). The spring 150 may retain the grip wedge 66 within the opening 64 of the load plate 54. For example, a first end of the spring 150 may be connected to the load plate 54 and an opposite end of the spring 150 may be connected to the grip wedge 66.

In an example construction, each load plate 54 may include a pair of spring straps 152 fastened (e.g., bolted) to each opposing major surface proximate an upper edge of the opening 64. Each spring strap 152 may be positioned in relative alignment with an associated grip wedge 66. For example, in the illustrated load balancing assembly 16 shown in FIGS. 5 and 6, each spring strap 152 is located above a corresponding grip wedge 66. An end of each spring strap 152 may extend past the upper edge of the opening 64 (FIGS. 5 and 6). A first pin 154 (FIG. 5) may be disposed within the opening 64 and may extend between opposing spring straps 152 (e.g., parallel spring straps 152 on opposing major surfaces of the load plate 54.

Each grip wedge 66 may include a second pin 156 (FIGS. 6 and 7) extending through the thickness direction (e.g., from side surface to side surface). Each grip wedge 66 may include at least one hole or channel 158 (FIG. 5) extending from a top surface to the second pin 156. The channel 158 may be suitably sized to receive a length of the spring 150. The first end of the spring 150 may be connected to the first pin 154 and the second end of the spring 150 may be connected to the second pin 156.

Referring to FIG. 9, during installation of coupon 11 to the load balancing assembly 16, the springs 150 may maintain the grip wedges 66 in position within the opening 64. For example, the springs 150 may prevent the grip wedges 66 from being removed from the opening 64 in the load plate 54 of the second (e.g., upper) load balancing assembly 16b by the force of gravity. Actuation of the adjusting mechanisms 98 (e.g., bolts 146) may act upon the grip wedges 66 of the second load balancing assembly 16b and against the springs 150 to move the grip wedges 66 with respect to the load plate 54 and position the grip wedges 66 in contact with the end surfaces of the coupon 11.

Alternatively, the adjusting mechanism 98 (e.g., bolts 146) may keep the grip wedges 66 in position within the opening 64 of the first (e.g., lower) load balancing assembly 16a acting against the force of gravity pulling the grip wedges 66 into the opening 64. Actuation of the adjusting mechanisms 98 (e.g., bolts 146) may act upon the grip wedges 66 of the first load balancing assembly 16a and against the force of gravity to move the grip wedges 66 with respect to the load plate 54 and position the grip wedges 66 in contact with the end surfaces of the coupon 11.

Position adjustment of the grip wedges 66 (e.g., by actuating the adjusting mechanism 98) may be performed by accessing only the second edge 60 of the load plate 54, thus allowing the plurality of load plates 54 to be positioned in close proximity to one another.

As the testing load is applied to the coupon 11 and increases (e.g., by moving the second load balancing assembly 16b along the axis of movement X with respect to the first load balancing assembly 16a), the coupon 11 may be pulled from the friction holder 104 (e.g., from between the pair of opposing grip wedges 66). As the coupon 11 is urged away from the direction of the testing load, the frictional engagement between the coupon 11 and the friction pads 140 may pull the grip wedges 66 outwardly from the opening 64, thus further closing the gap 68 and increasing the force being applied to the end of the coupon 11. Thus, as the testing load increases, the frictional load applied to the end of the coupon 11 also increases.

One skilled in the art can appreciate that other mechanisms may be utilized to initially retain the grip wedges 66 within the opening 64 of the load plate 54 and adjustably position the grip wedges 66 or friction pads 140 with respect to the opposing surfaces of the end of the coupon 11. For example, the friction holder 104 may include at least one cam lock mechanism, at least one hydraulically driven mechanism, or at least one rotatable louver mechanism to initially position the friction pad 140 in contact with the coupon 11 and allow the friction pad 140 to move in order to increase the frictional load applied to the surface of the coupon 11 as the testing load applied to the coupon 11 increases.

Figure 10:
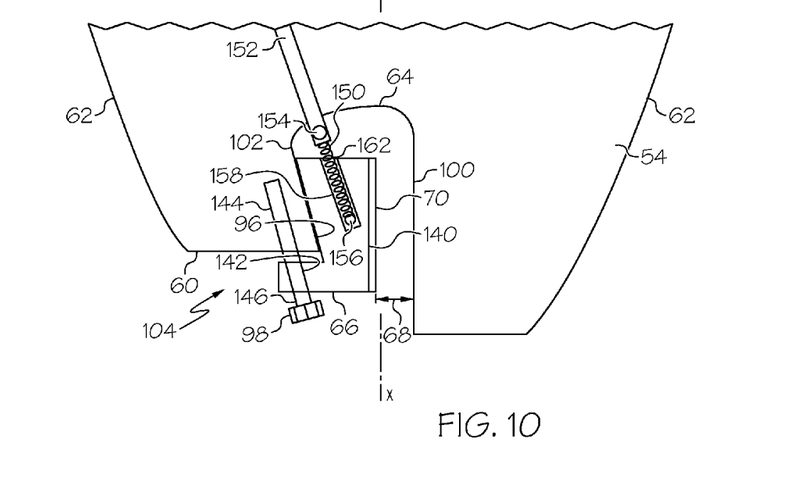
FIG. 10 is a side schematic view of another implementation of the friction holder of the disclosed apparatus for load testing a coupon.

Referring to FIG. 10, in another embodiment, each load plate 54 may include one grip wedge 66 adjustably connected within the opening 64. A first side surface 100 defining the opening 64 may include a substantially planar surface disposed substantially parallel to the axis of movement X. An opposing second side surface 102 defining the opening 64 may include a surface disposed at a non-zero angle with respect to the axis X for connection of the grip wedge 66. The first side surface 100 may be parallel to and face the first surface 70 (e.g., friction pad 140) of the grip wedge 66 defining the gap 68.

Upon actuation of the adjusting mechanism 98, the position of grip wedge 66 within the opening 64 and with respect to the first side surface 100 may be adjusted to adjust the gap 68. The coupon 11 (FIG. 1) may be frictionally retained between the first surface 100 defining the opening 64 and the first surface 70 of the grip wedge 66.

In use, the disclosed apparatus 10 may normally be oriented with the test frame 12 in a generally vertical orientation and a coupon 11 to be load tested being attached between opposing load balancing assemblies 14 as seen in FIG. 1. An operator (e.g., human, machine, or computer) may cause the load balancing assemblies 14 to move apart to apply a tensile load to the coupon 11 or to move together to apply a compressive load to the coupon 11. Movement may continue until a sufficient testing load has been reached or the coupon 11 has been destroyed. Alternatively, the disclosed apparatus 10 may be oriented with the test frame in a generally horizontal orientation.

Figure 11:
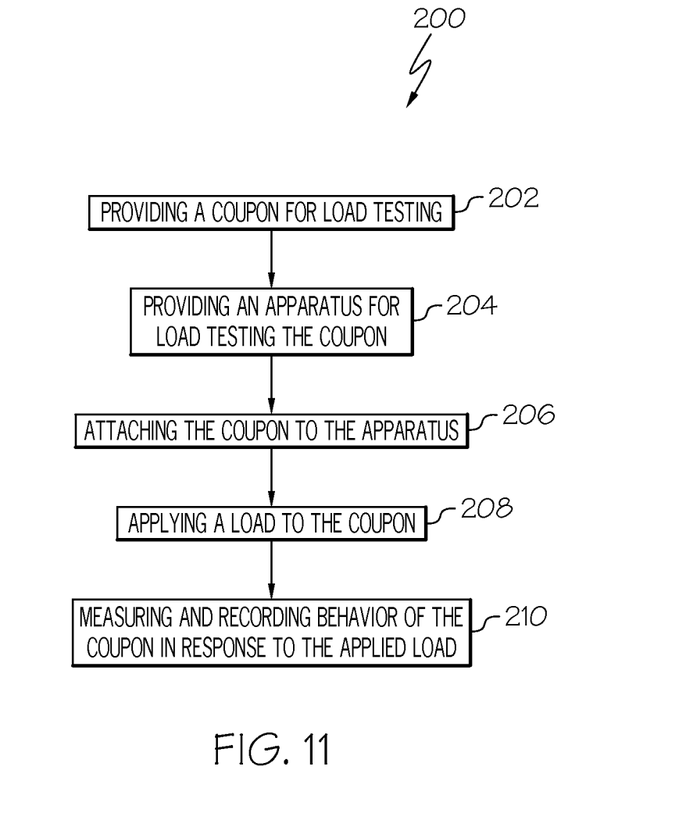
FIG. 11 is a flow diagram of the disclosed method for load testing a coupon.

Referring to FIG. 11, also disclosed is a method, generally designated 200, for load testing a coupon. As shown at block 202, a testing coupon may be provided for a sample material. For example, the coupon 11 (FIG. 1) may be a sample of composite material formed by any suitable process. The coupon 11 may include any number of laminate layers at any lay-up angle. The process for forming the coupons 11 may be automated, such as by machine or robot, to increase the speed of coupon fabrication. Since the coupon 11 does not require any special features configured for attachment of the coupon 11 to the disclosed load testing apparatus 10 (FIG. 1), fabrication complexity, cost, and time may be significantly decreased.

As shown at block 204, an apparatus (10 FIG. 1) for load testing a coupon may be provided. The apparatus 10 may include a test frame 12, at least one load assembly 14, and a pair of load balancing assemblies 16.

As shown at block 206, the coupon 11 may be attached to the testing apparatus 10. As discussed herein, the coupon 11 may be secured at each end by a load balancing assembly 16 (FIG. 1). The process of applying the coupon 11 to the load balancing assemblies 16 may be automated, such as by machine or robot, to increase the speed of insertion of the coupon 11.

As shown at block 208, a load may be applied to the coupon 11. As discussed herein, the load may be applied by linearly moving at least one load balancing assembly 16 along an axis of movement X with respect to an opposed load balancing assembly 16 (FIG. 1). For example, a tensile load may be applied to the coupon 11 by moving the load balancing assemblies 16 away from one another. As another example, a compressive load may be applied by moving the load balancing assemblies 16 toward one another. The process of applying the load to the coupon 11 may be automated, such as by machine or computer controlled control unit 48 (FIG. 4).

As shown at block 210, the behavior of the coupon 11 in response to the applied load may be recorded. For example, the strength properties of the sample material of the coupon may be determined under both a normal load and a peak (e.g., destructive) load. A strain gauge 49 (FIG. 4) may be used to measure and record the load applied during the test. The process of measuring and recording the load applied to the coupon 11 may be automated, such as by a computer.

Although various embodiments of the disclosed apparatus and method for load testing coupons have been shown and described, modifications may occur to those skilled in the art upon reading the specification. The present application includes such modifications and is limited only by the scope of the claims.

What is claimed is:

1. An apparatus for load testing a coupon, said apparatus comprising:
   a test frame; and
   an opposed pair of load balancing assemblies connected to said test frame, each load balancing assembly of said pair of load balancing assemblies comprising:
      a load leveling mechanism comprising:
         an arm; and
         a rigid lever comprising a first end and an opposed second end, said lever pivotally connected to said arm between said first end and said second end proximate a center of said lever; and
      a spaced apart plurality of load plates, each load plate of said plurality of load plates comprising a first end pivotally connected to an associated end of said lever and a second end; and
      a friction holder movably connected to said second end of said load plate and configured to frictionally engage an end of said coupon,
   wherein at least one load balancing assembly of said pair of load balancing assemblies is movable along an axis of movement with respect to an opposed load balancing assembly to communicate a load to said coupon, and
   wherein said load leveling mechanism equally distributes said load applied to said load balancing assembly through said lever and said plurality of load plates to said coupon.

2. The apparatus of claim 1 further comprising at least one load assembly connected to said at least one load balancing assembly of said pair of load balancing assemblies, said load assembly comprising a drive assembly operably engaged between said load assembly and said test frame and configured to move said load assembly along said axis of movement.

3. The apparatus of claim 1 further comprising at least one drive assembly operably engaged between said at least one load balancing assembly of said pair of load balancing assemblies and said test frame, said drive assembly being configured to move said at least one load balancing assembly of said pair of load balancing assemblies along said axis of movement.

4. The apparatus of claim 1 further comprising a pair of load assemblies, each load assembly of said pair of load assemblies being connected to one load balancing assembly of said pair of load balancing assemblies, each load assembly of said pair of load assemblies comprising a drive assembly operably engaged between said load assembly and said test frame and configured to move said load assembly along said axis of movement.

5. The apparatus of claim 1 further comprising a pair of drive assemblies, each drive assembly of said pair of drive assemblies being operably engaged between one load balancing assembly of said pair of load balancing assemblies and said test frame, each drive assembly of said pair of drive assemblies being configured to move said one load balancing assembly of said pair of load balancing assemblies along said axis of movement.

6. The apparatus of claim 1 wherein said load leveling mechanism further comprises a pair of rigid linkages, each linkage comprising a first end pivotably connected to said associated end of said lever and an opposed second end pivotably connected to said first end of said load plate.

7. The apparatus of claim 1 wherein
   said plurality of load plates comprises a first load plate and a second load plate,
   said load leveling mechanism further comprises:
      a rigid first linkage comprising a first end pivotably connected to said first end of said first lever and an opposed second end pivotably connected to said first end of said first load plate; and
      a rigid second linkage comprising a first end pivotably connected to said second end of said first lever and an opposed second end pivotably connected to said first end of said second load plate.

8. The apparatus of claim 1 wherein
   said lever is a rigid first lever,
   said plurality of load plates comprises a first load plate, a second load plate, a third load plate and a fourth load plate,
   said load leveling mechanism further comprises:
      a rigid first linkage comprising a first end pivotably connected to said first end of said first lever and an opposed second end;
      a rigid second linkage comprising a first end pivotably connected to said second end of said first lever and an opposed second end;
      a rigid second lever comprising a first end and an opposed second end, said second lever pivotably connected to said second end of said first linkage proximate a center of said second lever between said first end and said second end of said second lever;
      a rigid third lever comprising a first end and an opposed second end, said third lever pivotably connected to said second end of said second linkage proximate a center of said third lever between said first end and said second end of said third lever;
      a rigid third linkage comprising a first end pivotably connected to said first end of said second lever and an opposed second end pivotably connected to said first end of said first load plate;
      a rigid fourth linkage comprising a first end pivotably connected to said second end of said second lever and an opposed second end pivotably connected to said first end of said second load plate;
      a rigid fifth linkage comprising a first end pivotably connected to said first end of said third lever and an opposed second end pivotably connected to said first end of said third load plate;
      a rigid sixth linkage comprising a first end pivotably connected to said second end of said third lever and an opposed second end pivotably connected to said first end of said fourth load plate.

9. The apparatus of claim 8 wherein said load leveling mechanism comprises:
- a plurality of first levers pivotably connected to said arm;
- a plurality of first linkages connected to first ends of said plurality of first levers;
- a plurality of second linkages pivotably connected to second ends of said plurality of first levers;
- a plurality of second levers pivotably connected to second ends of said plurality of first linkages;
- a plurality of third levers pivotably connected to second ends of said plurality of second linkages;
- a plurality of third linkages pivotably interconnecting first ends of said plurality of second levers to said first end of said first load plate;
- a plurality of fourth linkages pivotably interconnecting second ends of said plurality of second levers to said first end of said second load plate;
- a plurality of fifth linkages pivotably interconnecting first ends of said plurality of third levers to said first end of said third load plate; and
- a plurality of sixth linkages pivotably interconnecting second ends of said plurality of second levers to said first end of said fourth load plate.

10. The apparatus of claim 1 wherein said friction holder comprises:
- an opening defined in said second end of each load plate; and
- at least one grip wedge adjustably connected to said load plate within said opening, said grip wedge being configured to frictionally engage a substantially planar surface of said coupon.

11. The apparatus of claim 10 wherein said friction holder comprises an adjusting mechanism configured to position said at least one grip wedge within said opening.

12. The apparatus of claim 11 wherein said friction holder comprises a connector configured to interconnect said at least one grip wedge and said load plate, said connector being configured to allow movement of said at least one grip wedge with respect to said load plate.

13. The apparatus of claim 1 wherein said load leveling mechanism further comprises:
- a first load distributing level comprising at least one rigid first lever pivotably connected to said arm proximate a center of said first lever; and
- a second load distributing level comprising at least two rigid second levers pivotably interconnecting said first lever and said plurality of load plates,
- wherein said first load distributing level equally distributes said load applied to said first load distributing level through said first lever to said second load distributing level as a first distributed load, and
- wherein said second load distributing level equally distributes said first distributed load applied to said second load distributing level through said second levers and said plurality of load plates to said coupon as a second distributed load.

14. A method for load testing a coupon, said method comprising:
- providing a test coupon;
- providing a pair of load balancing assemblies, each load balancing assembly comprising:
    - a load leveling mechanism comprising:
        - an arm; and
        - a rigid lever comprising an opposed pair of ends, said lever pivotably connected to said arm proximate a center of said lever between said pair of ends;
    - a spaced apart plurality of load plates, each load plate of said plurality of load plates comprising a first end pivotably connected to an associated end of said lever and a second end; and
    - a friction holder movably connected to said second end of said load plate and configured to frictionally engage an end of said coupon;
- connecting said coupon to said plurality of load plates between said pair of load balancing assemblies;
- applying a load to at least one load balancing assembly; and
- distributing said load equally through said lever and said plurality of load plates to said coupon.

15. The method of claim 14 wherein said load is a tensile load.

* * * * *